United States Patent [19]

Beuret et al.

[11] Patent Number: 4,808,294
[45] Date of Patent: Feb. 28, 1989

[54] PROBE FOR MEASURING THE PARTIAL PRESSURE OF OXYGEN IN A GASEOUS ATMOSPHERE IN RELATION TO A REFERENCE ATMOSPHERE

[76] Inventors: Pierre Beuret; Jacques Beuret, both of Route de Bure 21, Porrentruy, Switzerland, CH-2900

[21] Appl. No.: 36,756
[22] Filed: Apr. 10, 1987

[30] Foreign Application Priority Data
Apr. 17, 1986 [CH] Switzerland .................. 1543/86

[51] Int. Cl.⁴ .......................................... G01N 27/46
[52] U.S. Cl. ..................................... 204/427; 204/428
[58] Field of Search .................... 204/15, 421–429

[56] References Cited

U.S. PATENT DOCUMENTS

| | | | |
|---|---|---|---|
| 3,442,773 | 5/1969 | Wilson | 204/15 |
| 3,616,407 | 10/1971 | Engell et al. | 204/423 |
| 3,768,259 | 10/1973 | Carnahan et al. | 204/426 |
| 3,904,486 | 9/1975 | Faurscholi et al. | 204/422 |
| 3,940,327 | 2/1976 | Wagner et al. | 204/428 |
| 4,101,404 | 7/1978 | Blumenthal et al. | 204/428 |
| 4,141,812 | 2/1979 | Kawawa et al. | 204/422 |
| 4,193,857 | 3/1980 | Bannister et al. | 204/428 |
| 4,229,275 | 10/1980 | Habdas et al. | 204/426 |
| 4,339,318 | 7/1982 | Tanaka et al. | 204/428 |
| 4,537,661 | 8/1985 | Lee et al. | 204/1 T |
| 4,592,825 | 6/1986 | Crevoiserat | 204/428 |

Primary Examiner—T. Tung
Attorney, Agent, or Firm—Ralph W. Selitto, Jr.

[57] ABSTRACT

To make it possible to exchange the solid-electrolyte ball (1) easily and quickly, while at the same time ensuring effective sealing between the support (3) and the ball (1), when it has been polluted by the atmosphere of a furnace, the probe comprises a sleeve (4) communicating with the atmosphere of the furnace via orifices (13) and having a stop (5) forming a measuring electrode. The ball is stressed up against the stop (5) by a support (3), while a shoe (12) pressed against the ball (1) by a rod (9) forms an internal electrode. This rod (9) has a cavity (15), in which is accommodated a thermocouple (16) for measuring the temperature of the ball (1), and longitudinal ducts for the passage of wires (18, 19, 24) for connection to the thermocouple (16) and the shoe (12) and for conveying reference air into the region of the shoe. The spherical shape of the contact surface between the ball (1) and the support (3) ensures effective sealing.

15 Claims, 2 Drawing Sheets

PROBE FOR MEASURING THE PARTIAL PRESSURE OF OXYGEN IN A GASEOUS ATMOSPHERE IN RELATION TO A REFERENCE ATMOSPHERE

The subject of the present invention is a probe for measuring the oxygen partial pressure in a gaseous atmosphere in relation to a reference atmosphere, as defined in the pre-characterizing clause of the independent claim.

There are already several known types of probes, the reaction member of which comprises a zirconium pellet and which are sealed between the two atmospheres by means of a removable gasket or because the pellet is soldered to its support. However, the pellet remains expensive in terms of its production or maintenance. In fact, the pellet, at the end of its useful life, has to be replaced, together with its support if these two members are soldered together, or together with its gasket if such gaskets are used.

These probes are used for monitoring the atmospheres of heat-treatment furnaces, in which controlled austenitizing or cementation treatment is carried out. The reaction member is usually made of sintered zirconium and is stabilized with yttrium oxide. These reaction members can also be used for monitoring the combustion of heavy-oil and gas boilers or internal-combustion engines, in order to determine the ratio of carbon monoxide to carbon dioxide in the combustion gases or the exhaust gases.

For heat treatments, these probes are introduced directly into the treatment vessel and are subjected to highly variable temperatures and to very considerable thermal and mechanical shocks, the temperature variations ranging from ambient temperature to average temperatures of between 800° and 1250° C. Ceramic systems withstand these temperatures best. When platinum is used for the electrical contact of the external electrode or the gasket, the useful life of these members is limited because of the agressive behavior of soot towards platinum, and this makes it expedient to do without the gasket and platinum in the external measuring electrode.

The conditions which are important for the perfect functioning of such a measuring probe can be summarized as follows:

(1) Gas-tightness between the two zones of the reaction member, to prevent the atmosphere to be measured and the reference atmosphere from mixing with one another.

During operation, the treatment vessel may possibly be polluted by vapors from oil, salt or residues carried along by the components to be treated, even after these have been washed. Consequently, vapors can settle on the reaction member and result in a measuring error. Under such circumstances, it is necessary to burn these impurities or quickly exchange the reaction and sealing member, this being a very costly operation.

(2) Ensuring gas-tightness without using either a gasket or adhesive material.

(3) Electrical insulation between the two zones of the reaction member (gas to be measured and reference gas), to make it possible to produce an electrical potential difference and avoid a short-circuit caused by the use of a metallic support.

(4) Easy interchangeability of the reaction member.

The known probes are nowhere near meeting these conditions.

French Patent Application No. 77.14 400 describes a measuring cell which makes it possible to determine the oxygen concentration in a gaseous mixture. A frustoconical insert is put in direct contact with a metal casing and a sleeve made of aluminium oxide. It would not be possible for this measuring cell to function satisfactorily, because the contact surfaces between the insert, on the one hand, and the metal casing and aluminium oxide sleeve, on the other hand, cannot ensure the requisite sealing. In fact, the different expansions of the parts mentioned above must necessarily result in the formation of leaks which would make the cell in question useless. The use of a metallic support will inevitably imply the risk of a short-circuit.

U.S. Pat. No. 4,339,318 also relates to a device for analyzing a gas containing oxygen. The insert in the form of a cylindrical disk is placed in a shoulder forming the transition between two cylindrical bores of different diameters. The required sealing can obviously only be ensured by using an adhesive material; moreover, the insert is not interchangeable.

U.S. Pat. No. 3,616,407 shows a device for determining the oxygen content of metals in the liquid state. This proposes a spherical electrolyte placed in a spherical seat formed in the front part of a tube. The spherical electrolyte, which clearly has to be fitted in the malleable state before baking the ceramic material, is not interchangeable, and its seat will have gas leaks caused as a result of the different thermal expansion of the tube in relation to that of the electrolyte. Moreover, the device described is unsuitable for measuring the partial pressure of oxygen in a gaseous atmosphere.

The object of the invention is to make it easier to exchange the reaction member, whilst at the same time ensuring effective sealing without the use of a gasket or an adhesive material.

This object is achieved by means of the combination of elements as described in the characterizing clause of the independent claim.

The accompanying drawing illustrates, by way of example, an embodiment of the probe and several alternative forms:

FIGS. 1 and 2 illustrate a probe for the continuous measurement of the partial pressure of oxygen in a gaseous atmosphere in relation to air chosen as a reference atmosphere.

Figure 1:
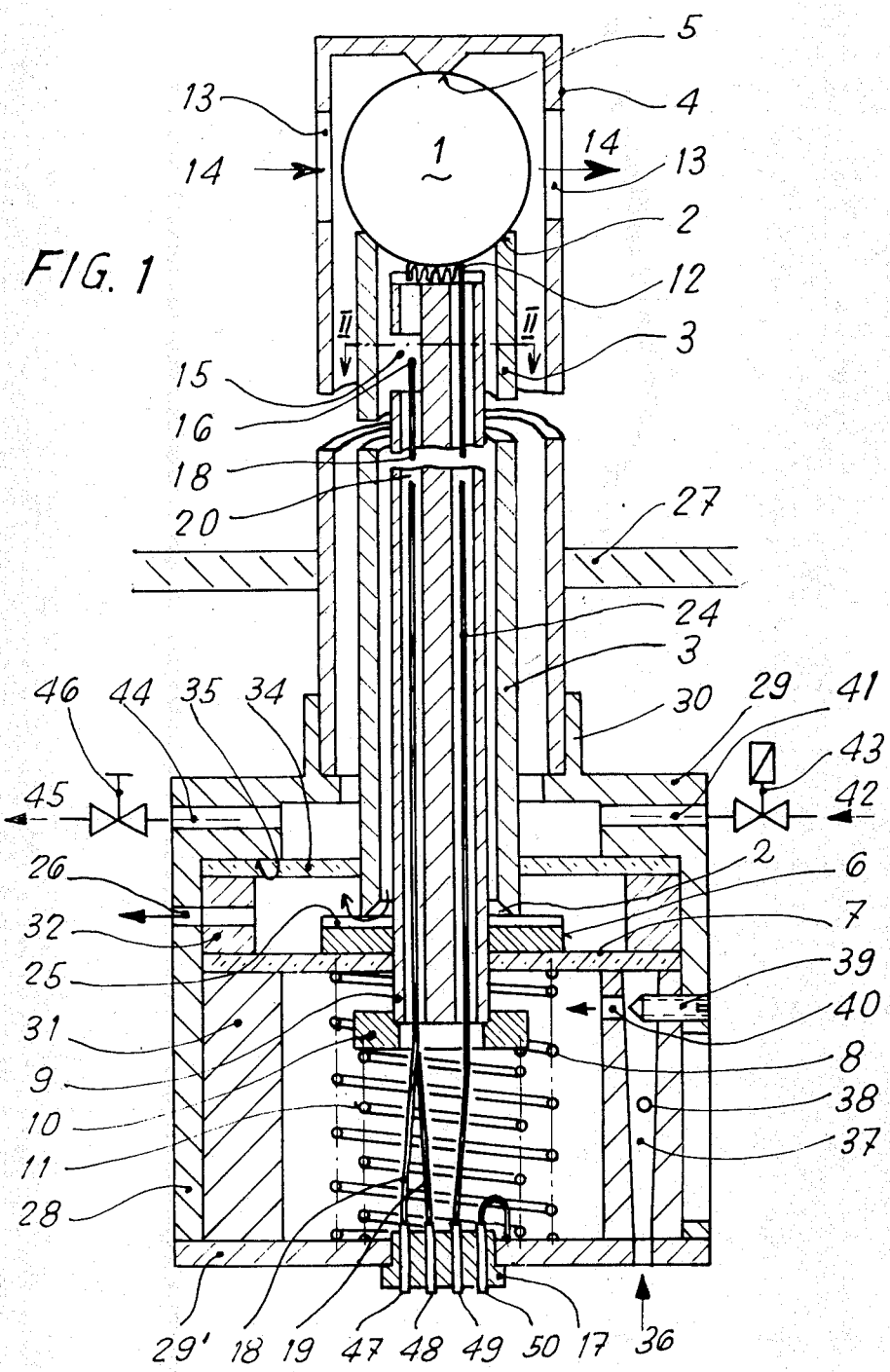
FIG. 1 is a cutaway view in axial section of an embodiment of the probe.

It comprises a reaction member 1 in the form of a solid electrolyte ball composed of sintered and stabilized zirconium oxide. This ball rests on the sealed seat 2 of a ceramic support 3. A sleeve 4 made of refractory steel and acting as an external electrode has an inner projection 5 forming a stop, whilst the other end of the support 3 is fixed to a washer 6 interacting with an airtight diaphragm 7 and a spring 8. This arrangement makes it possible to keep the ball 1 in place with the requisite pressures between the latter, on the one hand, and the seat 2 and stop 5, on the other hand. A rod 9 located inside the support 3 and forming an internal electrode carries a washer 10 interacting with a spring 11, the other end of the rod 9 pressing a contact shoe 12 against the ball 1. The assembly formed by the ball 1, the seat 2, the stop 5 and the shoe 12 constitutes the measuring head.

Figure 2:
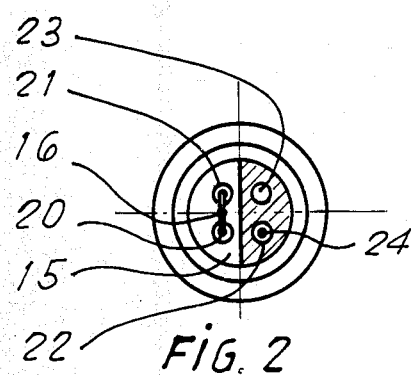
FIG. 2 is a sectional view according to II—II of FIG. 1.

The end of the sleeve 4 has orifices 13 for the passage of the gas to be measured 14. It will be seen in FIG. 1 that the contact surface between the ball 1 and the sealed seat 2 of the support 3 does not have any gasket. Rather, the sealed seat 2 is in the form of an endless bevelled surface having a contour which matches the contour of the abutting portion or contact surface of the reaction member 1, thereby forming a washerless gastight seal. As can be seen better in FIG. 2, the inner rod 9 has a chamber 15, in which is accommodated a thermocouple 16 connected to two corresponding terminals of a connector 17 by means of two wires 18, 19 passing longitudinally through the rod 9 along two corresponding ducts 20, 21. The inner rod 9 has two other longitudinal ducts 22, 23. A wire 24 connecting the shoe 12 to the connector 17 passes through the duct 22. The duct 23 makes it possible to supply reference air which sweeps over the lower face of the ball 1 and escapes between the inner rod 9 and the support 3 and then through an orifice 25 in the washer 6 and an orifice 26 in a housing which will be described later. The end of the sleeve 4 containing the head of the probe is intended to be engaged, for example, into the measuring vessel of a heat-treatment furnace, the atmosphere of which is to be measured, the sleeve entering this vessel via a wall 27.

The probe also has a sealed housing 28 composed of a casing 29 carrying a collar 30, into which the sleeve 4 is screwed, and of a removable cover 29'. The sealed diaphragm 7 already mentioned is gripped between two rings 31 and 32, whilst a second sealed diaphragm 34 is gripped between the ring 32 and a flat region 35 of the interior and the casing 29 of the housing. The cover 29', in addition to carrying the connector 17 already mentioned, has an inlet 36 for the reference air, this inlet communicating with the flow meter 37 which is arranged in the ring 31 and which comprises a float 38 and a needle screw 39 for presetting the flow rate. This reference air enters the space delimited under the diaphragm 7 via an orifice 40 in the flow meter, and then follows the path described above, which ends in the space delimited between the two diaphragms 7 and 34 and the orifice 26 made in the ring 32 and the casing 29. The latter has an orifice 41 cooperating with an additional air inlet which is represented diagrammatically at 42 and which is controlled by a solenoid valve 43, in order to bleed and burn sporadically the possible impurities contained in the measuring head. The casing 29 also has an outlet orifice 44 cooperating with an orifice shown diagrammatically at 45 and controlled by a valve 46, in order to extract samples of the treatment gases and analyze them.

The connector 17 is intended to be connected directly to an electronic monitoring or regulating unit (not shown). For this purpose, it has four pins 47, 48, 49, 50, of which the first two are connected respectively to the wires 18, 19 of the thermocouple 16, the pin 49 is connected to the negative-bias wire 24 of the internal electrode 9 and the positive pin 50 is connected to the housing 28. The probe operates as follows: the voltage generated by the thermocouple 16 at the terminals 47, 48 represents in millivolts the temperature of the gas 14 to be measured. The voltage generated between the terminals 49 and 50, that is to say between the external and internal electrodes in direct contact with the reaction member 1, represents the oxygen concentration in millivolts according to the Nernst equation and in direct proportion to the carbon potential, for the purpose of regulating the heat-treatment atmospheres. Experience has shown us that the measuring accuracy obtained by means of the above-described probe is higher than that obtained by means of conventional probes.

For the maintenance or exchange of the reaction member 1, it is sufficient to unscrew the sleeve 4 from the housing 28 by means of the thread (not shown) provided in the collar 30, and remove this reaction member from the support 3 in order to expose the measuring-head assembly. Accessibility and maintenance become much simpler as a result.

Figure 3:
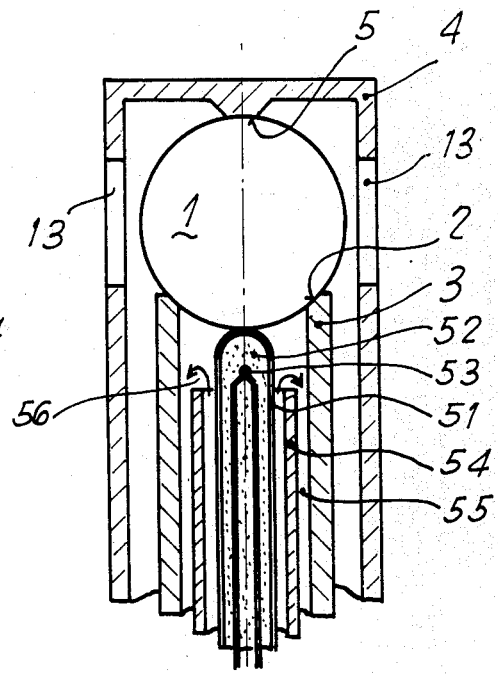
FIGS. 3, 4 and 5 show alternative forms of the measuring head.

The alternative form illustrated in FIG. 3, where the reference numerals already used represent components identical to those of the embodiment described above, comprises a metal tube 51 as an internal electrode, which is filled with magnesium oxide 52 and which bears elastically against the ball 1 by means of its rounded upper end. This tube 51 contains a thermocouple 53 connected by means of two wires to the pins 47, 48 of a connector not shown in this FIG. 3, but identical to that 17 of FIG. 1, this thermocouple performing the same function as before.

The metal tube 51 is connected to the pin 49. This tube 51 is seated concentrically in a tube 54, with a passage 55 for conveying the reference air 56 up against the ball being formed between the two.

Figure 4:
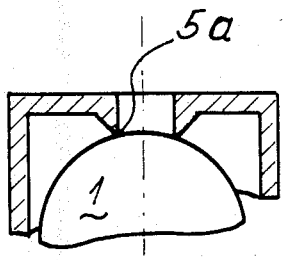

FIG. 4 shows an alternative form 5a of the stop 5 of the sleeve 4, which improves electrical contact between the latter and the reaction member 1.

Figure 5:
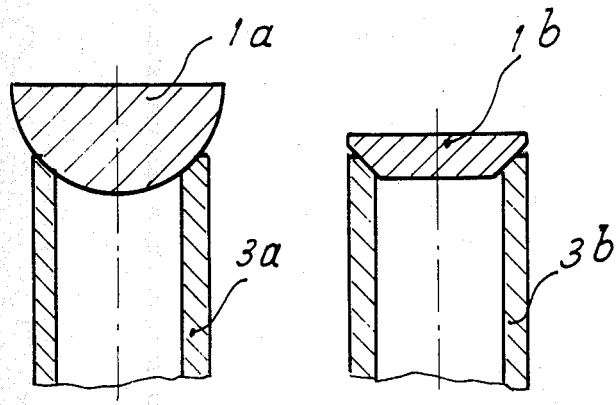

FIG. 5 illustrates two possible alternative forms 1a, 1b of the reaction member 1, and the corresponding alternative forms 3a, 3b of the support 3.

According to another alternative form, the two ends of the tubular support 3 can be equipped with spherical seats 2 (FIG. 1), so that the tubular support 3, once damaged or worn, can be reversed and consequently has a remarkably long useful life.

We claim:

1. A probe for measuring the partial pressure of oxygen in a gaseous atmosphere in relation to a reference atmosphere, comprising:

a solid-electrolyte reaction member having a shape which is symmetrical about a plane containing an axis of rotation of said reaction member, said shape being such that said reaction member has a widest portion;

a support tube having a diameter, said support tube being made from ceramic and including first supporting means located at an open end of said support tube supporting said reaction member on one side thereof and an interior chamber connecting said open end of said support tube to an opposite end of said support tube, whereby the reference atmosphere can flow through said interior chamber of said support tube and contact said reaction member;

a sleeve disposed coaxially about said support tube and in spaced relationship thereto such that an annular passageway is formed between said sleeve and said support tube, one end of said sleeve being closed and having second supporting means supporting said reaction member on an opposite side thereof, said sleeve including orifices which are aligned with said reaction member so as to permit the gaseous atmosphere to flow into said annular passageway and contact said reaction member and said sleeve being removable from said support tube, whereby said sleeve can be removed in order to permit the replacement of said reaction member; and urging means for urging said support tube towards said reaction member such that said first supporting means is pressed into direct contact with an abutting portion of said reaction member so as to cause said reaction member and said first supporting means to cooperate with each other and with each other only to form a washerless gas-tight seal between said annular passageway and said interior chamber of said support tube, whereby the gaseous atmosphere is separated from the reference atmosphere by said seal, said first supporting means including an endless bevelled surface having a contour which matches the contour of said abutting portion of said reaction member to form a positive seat for said reaction member and thereby facilitate the formation of said seal, said bevelled surface being formed in a terminal edge of said open end of said support tube such that said widest portion of said reaction member is located externally of said support tube, and said widest portion of said reaction member being wider than said diameter of said support tube.

2. A probe according to claim 1, wherein said contour of said abutting portion of said reaction member is in the form of a spherical surface and wherein said bevelled surface has a matching annular curved shape.

3. A probe according to claim 2, wherein said reaction member is in the form of a sphere made from sintered and stabilized zirconium oxide and wherein said bevelled surface has a radius of curvature which is the same as the radius of said sphere.

4. A probe according to claim 1, wherein said contour of said abutting portion of said reaction member is in the form of a tapered surface and wherein said bevelled surface has a matching tapered shape.

5. A probe according to claim 4, wherein said reaction member is in the form of a truncated cone made from sintered and stabilized zirconium oxide.

6. A probe according to claim 1, wherein said support tube is reversible and wherein said opposite end of said support tube is open and includes third supporting means for supporting said reaction member on said one side thereof, whereby said support tube can be removed and reversed such that said reaction member is supported by said third supporting means rather than by said first supporting means.

7. A probe according to claim 6, wherein said opposite end of said support tube is identical to said open end of said support tube, whereby said first and third supporting means can be used interchangeably to support said reaction member without having to replace said support tube or said reaction member.

8. A probe according to claim 6, further comprising a housing, said support tube and said sleeve being removably attached to said housing.

9. A probe according to claim 8, wherein said probe is attached to a heat-treatment furnace such that said housing is located externally of said furnace and said reaction member is located internally of said furnace, whereby the gaseous atmosphere is the atmosphere within said furnace.

10. A probe according to claim 9, wherein said interior chamber of said support tube communicates with said housing, whereby the reference atmosphere can be supplied to said interior chamber through said housing.

11. A probe according to claim 10, wherein said annular passageway communicates with said housing, whereby samples of the gaseous atmosphere can be taken through said housing.

12. A probe according to claim 1, wherein said sleeve is made from refractory steel and functions as an external electrode and wherein said support tube houses an internal electrode and a conductive shoe which is resiliently urged against said reaction member by said internal electrode.

13. A probe according to claim 12, wherein said axis of rotation of said reaction member is coaxially arranged with respect to said support tube and wherein said second supporting means and said shoe are arranged along said axis of rotation on opposite sides of said reaction member from each other.

14. A probe according to claim 1, wherein said closed end of said sleeve has a centrally located opening which extends through said second supporting means such that said second supporting means is provided with an endless contact edge against which said reaction member is urged by said urging means.

15. A probe according to claim 1, wherein said sleeve is made from refractory steel and functions as an external electrode and wherein said support tube houses an internal electrode, including a metal tube which is filled with magnesium oxide and which has a closed end containing a thermocouple, said closed end of said metal tube being resiliently urged against said reaction member.

* * * * *